United States Patent [19]

Baker

[11] Patent Number: 5,387,394

[45] Date of Patent: Feb. 7, 1995

[54] OPHTHALMIC COMPOSITIONS AND METHODS FOR PRESERVING AND USING SAME

[75] Inventor: John C. Baker, Irvine, Calif.

[73] Assignee: Allergan, Inc., Irvine, Calif.

[21] Appl. No.: 59,522

[22] Filed: May 11, 1993

Related U.S. Application Data

[63] Continuation of Ser. No. 905,628, Jun. 29, 1992, abandoned.

[51] Int. Cl.$^6$ ............... A01N 25/02; A61L 2/18
[52] U.S. Cl. ..................... 422/28; 514/840; 424/78.04; 424/405
[58] Field of Search ........... 422/28, 905; 134/901; 252/106, 173, 174.12, 174.23, DIG. 5, DIG. 12, DIG. 13, 407; 424/78.04, 405, 632; 514/839

[56] References Cited

U.S. PATENT DOCUMENTS

| | | | |
|---|---|---|---|
| Re. 32,672 | 5/1988 | Huth et al. | 252/106 X |
| 3,830,913 | 8/1974 | Harich | 424/195.1 |
| 3,852,436 | 12/1974 | Harich | 424/195.1 |
| 3,890,212 | 6/1975 | Harich et al. | 424/195.1 |
| 4,021,577 | 5/1977 | Harich et al. | 424/195.1 |
| 4,356,100 | 10/1982 | Sherman | 252/106 |
| 4,485,029 | 11/1984 | Kato et al. | 252/106 |
| 4,560,491 | 12/1985 | Sherman | 422/28 X |
| 4,941,995 | 7/1990 | Richards | 252/407 |
| 5,190,979 | 3/1993 | Herman | 514/859 X |

OTHER PUBLICATIONS

JP Abstract, A,3 090 008, Apr. 16, 1991.

*Primary Examiner*—Robert J. Warden
*Assistant Examiner*—E. Leigh Dawson
*Attorney, Agent, or Firm*—Frank J. Uxa

[57] ABSTRACT

Ophthalmic compositions, such as those used to care for contact lenses, methods of preserving such compositions, and methods for disinfecting contact lenses using such compositions are disclosed. The compositions may comprise an ophthalmically acceptable, liquid aqueous medium and, included therein, an effective preserving or disinfecting amount of grapefruit seed extract.

20 Claims, No Drawings

OPHTHALMIC COMPOSITIONS AND METHODS FOR PRESERVING AND USING SAME

This application is a continuation of application Ser. No. 07/905,628, filed Jun. 29, 1992, now abandoned.

BACKGROUND OF THE INVENTION

This invention relates to ophthalmic compositions and methods for preserving and using such compositions. More particularly, the present invention relates to ophthalmic compositions, e.g., useful in caring for contact lenses, which include grapefruit seed extract as a preservative or disinfectant, and to methods for disinfecting contact lenses using such compositions.

Various compositions, e.g., solutions, are used in association with contact lenses to ensure that the lenses may be safely, comfortably and conveniently worn. Contact lens care compositions, for example, disinfecting compositions, preserving compositions, cleaning compositions, wetting compositions, conditioning compositions and the like, often utilize at least one disinfectant or at least one preservative, depending on the type of composition, for disinfecting or preserving contact lenses after wear or preserving the lens care composition itself. A contact lens disinfecting composition generally has sufficient antimicrobial activity so that when the composition is contacted with a lens to be disinfected, microorganisms associated with the lens are killed or otherwise removed and the contact lens is effectively disinfected within a reasonable time, e.g., in the range of about 0.1 hour to about 12 hours. A contact lens disinfecting composition may be termed a microbio-cidal composition. In contrast, a preserved contact lens care composition has sufficient antimicrobial activity, often less of such activity than is present in a contact lens disinfecting composition, so that when the composition is contacted with a contact lens substantially no increase in the microorganism population on the lens or in the composition is obtained. A preserved contact lens care composition may be termed a microbio-static composition. Contact lens care compositions are preserved to prevent any substantial increase in the population of contaminating microorganisms in the compositions and, thereby, to extend their shelf life. Some preservatives used in preserved compositions may also be used as disinfecting agents in lens disinfecting compositions.

Various synthetic compounds are known for use as preserving agents in preserved contact lens care compositions. Examples include thimerosal, benzalkonium chloride and chlorhexidine. However, these synthetic preserving agents are known to exhibit ocular toxicity which may result in irritation or sensitivity to the eye. The degree of ocular toxicity increases when these agents are utilized as disinfecting agents. Further, a soft contact lens, a rigid gas permeable contact lens (RGP) or a hard contact lens can absorb or adsorb these compounds. This causes the contact lens to retain the irritating compound and contributes to the eye irritation and sensitivity which may result.

Other conventional methods of contact lens chemical disinfection utilize one or more active disinfecting agents in an aqueous medium, for example, a chlorhexidine/thimerosal solution or a relatively mild solution of hydrogen peroxide. Some of these disinfecting solutions, such as those named above, are cytotoxic and are known to be adsorbed or absorbed onto or into a contact lens and cause the lens to elicit a cytotoxic response after disinfection. For example, contact lenses which have been soaked in a disinfecting hydrogen peroxide solution are to be treated to remove residual hydrogen peroxide, e.g., by soaking in a catalase solution, before they may be comfortably and safely worn again. If residual hydrogen peroxide remains on the lenses, then irritation or injury to the eye may result.

Thus, it is readily apparent that a continuing need exists for safe and efficacious compositions that can be used as contact lens disinfecting compositions and as preserved contact lens care compositions.

SUMMARY OF THE INVENTION

New disinfecting and preserved compositions and methods, particularly such compositions and methods directed to contact lens care, have been discovered. The present compositions include effective disinfectants and/or preservatives. Thus, for example, a contact lens can be effectively disinfected in a reasonable length of time. Also, contact lens care products can be effectively preserved against growth of contaminating microorganisms. Importantly, such disinfecting and preserving activities are achieved and the contact lenses disinfected or otherwise cared for using the present compositions can be safely and comfortably worn with little or no risk of eye irritation or sensitivity, e.g., from the presence of residual disinfectant/preservative.

In one broad aspect of the invention, a composition, preferably a substantially non-oxidative composition, useful for disinfecting a contact lens is provided. This composition includes a medium, preferably a liquid aqueous medium. Included within this medium is an effective disinfecting amount of grapefruit seed extract. Methods of disinfecting a contact lens include contacting the lens to be disinfected with an appropriate grapefruit seed extract-containing composition, as described herein. Such grapefruit seed extract is an effective disinfectant in the contact lens care context without the need for oxidizing agents.

Preserved compositions, e.g., contact lens care compositions, which include an ophthalmically acceptable medium, preferably containing one or more components effective to beneficially affect a contact lens and/or the wearing of a contact lens, are included within the scope of the present invention. Such preserved compositions which are preferably substantially non-oxidative, include an effective preserving amount of grapefruit seed extract. Contact lenses which are disinfected or otherwise treated using the present compositions can be safely and comfortably worn with little or no risk of eye irritation or sensitivity.

DETAILED DESCRIPTION OF THE INVENTION

The present invention is applicable to disinfecting all types of lenses, e.g., contact lenses, which are benefited by such disinfecting. Such lenses, e.g., conventional soft contact lenses, RGPs and hard contact lenses, may be made of any suitable material or combination of materials and may have any suitable configuration. The invention is also applicable to preserving compositions, such as contact lens care compositions, and other eye care products which are benefited by being preserved.

One important feature of the substantially non-oxidative compositions of the present invention is the inclusion of an effective, e.g., for disinfecting and/or preserving, amount of grapefruit seed extract. Without wishing to limit the invention to any particular theory of operation, it is believed that the grapefruit seed extract useful in the present invention is sufficiently active to provide the desired degree of disinfecting or preserving without causing substantial eye irritation or sensitivity.

As used herein, "grapefruit seed extract" refers to one or more components, in particular one or more antimicrobial components, derived from grapefruit seeds by extraction, and/or the like processing technique, using an organic solvent, such as an organic solvent containing one or more hydroxyl groups, for example glycols. A commercially available product sold under the name "grapefruit seed extract" is formed by extracting the seeds of grapefruit with propylene glycol and/or glycerine. Its recommended application is as a preservative in the cosmetic industry and has been assigned FDA No. R 0013982. This commercially available product is useful in the present invention. "Grapefruit seed extract" is an approved name for designation of ingredients for cosmetics under the Food and Drug Administration, 21 CFR 701.3(c)(2)(i), being defined in the Cosmetic Ingredient Dictionary. The antimicrobially active components of grapefruit seed extract are preferably soluble in propylene glycol and/or glycerine. This extract often includes various naturally occurring salts of ascorbic acid, as well as various other naturally occurring compounds, including fruit sugars, glucine (an amino acid) and vitamin E. Certain "essential oils" have been shown to exhibit antimicrobial activity. A definition of essential oils and a description of their activity appears in M. deNavarre Chemistry and Manufacture of Cosmetics, Second Edition, 1975, Vol. III, pp. 85-109. See also 46 Agricultural Biological Chemistry 1655-1660(1982). Without wishing to limit the invention to any particular theory of operation, grapefruit seed extract may contain essential oils which exhibit antimicrobial activity in the present context.

Since contact lens disinfecting compositions and other contact lens care compositions are most often solutions, the grapefruit seed extract is preferably soluble in the media, preferably the liquid aqueous media, which are included in the present compositions. The amount of grapefruit seed extract employed in the present compositions is that sufficient to obtain the desired result. Care should be taken to avoid excessive amounts of grapefruit seed extract. The use of large excesses of grapefruit seed extract may result in some degree of eye irritation and/or sensitivity. The presently useful grapefruit seed extract is preferably present in an amount in the range of about 0.001% to about 1% or about 5%, by weight per volume of the total composition.

The present compositions may include other, e.g., complementary and/or potentiating, antimicrobial agents. Examples of such other antimicrobial agents include, but are not limited to, thimerosal, sorbic acid, 1.5-pentanedial, alkyl triethanolamines, boric acid, ophthalmically acceptable salts of any of the above, 3-chloroallyl-3, 5, 7, triaza-1-azonia adamantine chloride, phenylmercuric salts and mixtures thereof. Ophthalmically acceptable salts may include one or more ophthalmically acceptable anions, e.g., chloride ($Cl^-$), bromide, iodide, bisulfate, phosphate, acid phosphate, nitrate, acetate, maleate, fumarate, oxalate, lactate, tartrate, citrate, gluconate, saccharate, p-toluene sulfonate and the like, as noted above, or ophthalmically acceptable cations, in particular alkali and alkali metal cations. Materials which provide more than one beneficial or desired property to the present compositions may also be included. For example, certain combinations of quaternary ammonium compounds which possess both antimicrobial activity and wetting properties may be included. Examples of such combinations of quaternary ammonium compounds include, but are not limited to, balanced mixtures of N-alkyl dimethyl benzyl ammonium chlorides and N-alkyl dimethyl ethylbenzyl ammonium chlorides. Each of these agents/materials may be included in the present compositions in an amount effective to provide the beneficial or desired property or properties.

The compositions of the present invention preferably include an ophthalmically acceptable medium, more preferably an ophthalmically acceptable liquid aqueous medium. This medium often acts as a carrier, e.g., as a solvent, for the other components in the composition. A material is "ophthalmically acceptable" if the material can be placed into a mammalian eye without causing any substantial damage or harm to the eye. One particularly useful ophthalmically acceptable medium is water. Preferably, the medium, and in fact the entire composition, is sterile.

In certain embodiments, the present compositions advantageously include at least one ophthalmically acceptable polymeric wearability component in an amount effective to act on a contact lens contacted by such composition so as to enhance the wearability of the contact lens in the mammalian eye. Such wearability components may wet (or rewet) the lens, condition the lens, coat the lens or otherwise interact with the lens to provide the wearer of the lens with an increased degree of lens wearing comfort relative to wearing a contact lens treated with a substantially identical composition without the wearability component. The wearability component is a polymeric component, that is, a component which has one or more sub-molecular units which are repeated at least once, preferably at least about 10 times, in each molecule of the polymeric wearability component.

Among the useful polymeric wearability components which may be included in the present compositions are contact lens wetting (or rewetting) agents, contact lens conditioning agents and the like. Many such agents are conventional and well known in the art of contact lens care.

Useful polymeric contact lens wetting (or rewetting) agents and conditioning agents include, but are not limited to, polyvinyl alcohol, polyoxamers, polyoxyalkylene polymers and copolymers, polyvinyl pyrrollidine, hydroxypropyl methyl cellulose, hydroxyethyl cellulose, other ophthalmically acceptable cellulose derivatives, ophthalmically acceptable nonionic surfactants, and mixtures thereof.

The wearability component or components are included in the present compositions in an amount effective to impart or provide the desired increase in lens wearability. Such amount or amounts may vary widely depending, for example, on the specific composition being employed, the specific wearability component or components being utilized, the specific wearability result desired and the composition of the contact lens with which the composition is to be utilized. Preferably, the polymeric wearability component is present in an amount in the range of about 0.1% to about 4%, more preferably about 0.3% to about 3%, (weight/volume) of the composition.

One or more additional components can be included in the present compositions based on the particular application for which the compositions are formulated. Thus, the present compositions can be formulated as disinfecting compositions, cleaning compositions, wetting compositions, conditioning compositions, soaking compositions and the like. Also, the present compositions can be formulated to be useful in performing two or more contact lens caring operations. For example, a disinfecting/cleaning composition, or a cleaning/conditioning composition or even an all purpose lens care composition can be formulated and such multi-functional compositions are included within the scope of the present invention.

The additional component or components included in the present compositions are chosen to impart or provide at least one beneficial or desired property to the compositions. Such additional components may be selected from components which are conventionally used in one or more contact lens care compositions. Examples of such additional components include buffering agents, cleaning agents, wetting agents, for example, surfactants, nutrient agents, sequestering agents, viscosity builders, tonicity agents, contact lens conditioning agents, antioxidants, pH adjustors, and the like. These additional components may each be included in the present compositions in an amount effective to impart or provide the beneficial or desired property to the compositions. For example, such additional components may be included in the present compositions in amounts similar to the amounts of such components used in other, e.g., conventional, contact lens care products.

Useful buffering agents include, but are not limited to, acetate buffers, citrate buffers, phosphate buffers and borate buffers. Acids and bases may be used to adjust the pH of the present compositions as needed.

Useful sequestering agents include, but are not limited to, disodium ethylene diamine tetraacetate, alkali metal hexametaphosphate, citric acid, sodium citrate and mixtures thereof.

Useful tonicity adjustors include, but are not limited to, sodium chloride, potassium chloride, mannitol, dextrose, glycerin, propylene glycol and mixtures thereof.

Useful viscosity builders include, but are not limited to, hydroxyethyl cellulose, hydroxymethyl cellulose, polyvinyl pyrrolidone, polyvinyl alcohol and mixtures thereof.

Useful antioxidants include, but are not limited to, sodium metabisulfite, sodium thiosulfate, N-acetylcysteine, butylated hydroxyanisole, butylated hydroxytoluene and mixtures thereof.

In a particularly useful embodiment, the grapefruit seed extract-containing compositions further include at least one enzyme effective to remove debris from a contact lens. Among the types of debris that form on a contact lens during normal use are protein-based debris, mucin-based debris, lipid-based debris and carbohydrate-based debris. One or more types of debris may be present on a single contact lens.

The enzyme employed may be selected from enzymes which are conventionally employed in the enzymatic cleaning of contact lenses. For example, many of the enzymes disclosed in Huth et al U.S. Pat. RE No. 32,672 and Karageozian et al U.S. Pat. No. 3,910,296 are useful in the present invention. Each of these patents is incorporated in its entirety by reference herein. Among the useful enzymes are those selected from proteolytic enzymes, lipases and mixtures thereof.

Preferred proteolytic enzymes are those which are substantially free of sulfhydryl groups or disulfide bonds. Metallo-proteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Asperigillus molds. Within this grouping, the still more preferred enzymes are the derived alkaline proteases generically called subtilisin enzymes. Reference is made to Deayl, L., Moser, P. W. and Wildi. B. S., "Proteases of the Genus Bacillus, II Alkaline Proteases", Biotechnology and Bioengineering, Vol. XII, pp 213–249 (1970) and Keay, L. and Moser, P. W., "Differentiation of Alkaline Proteases form Bacillus Species" Biochemical and Biophysical Research Comm., Vol 34, No. 5, pp 600–604, (1969).

The subtilisin enzymes are broken down into two sub-classes, subtilisin A and subtilisin B. In the subtilisin A grouping are enzymes derived from such species as *B. subtilis, B. licheniformis* and *B. pumilis*. Organisms in this sub-class produce little or no neutral protease or amylase. The subtilisin B sub-class is made up of enzymes from such organisms as *B. subtilis, B. subtilis var. amylosacchariticus, B. amyloliquefaciens* and *B. subtilis* NRRL B3411. These organisms produce neutral proteases and amylases on a level about comparable to their alkaline protease production. One or more enzymes from the subtilisin A sub-class are particularly useful.

In addition other preferred enzymes are, for example, pancreatin, trypsin, collaginase, keratinase, carboxylase, aminopeptidase, elastase, and aspergillo-peptidase A and B, pronase E (from *S. griseus*) and dispase (from *B. polymyxa*).

An effective amount of enzyme is to be used in the practice of this invention. Such amount will be that amount which effects removal in a reasonable time (for example overnight) of substantially all of at least one type of debris from a lens due to normal wear. This standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective cleaner will depend on several factors, including the inherent activity of the enzyme, and the excipient it contains.

As a basic yardstick, the working solution should contain sufficient enzyme to provide about 0.001 to about 3 Anson units of activity, preferably about 0.01 to about 1 Anson units, per single lens treatment. Higher or lower amounts may be used.

Enzyme activity is pH dependent. Thus, for any given enzyme, there is a particular pH range in which that enzyme will function best. The determination of such range can readily be done by known techniques.

The present compositions may be used in the care of a contact lens, e.g., to disinfect the lens, to preserve the lens, to otherwise treat the lens and/or to make wearing the lens safe and comfortable. The present compositions, formulated appropriately, may be used in conventional contact lens care regimens by using the present compositions in place of prior conventional compositions. In many instances, these contact lens care regimens involve contacting the lens with the present composition in an amount, and at conditions, effective to obtain the beneficial or desired contact lens care result. For example, a contact lens to be disinfected may be contacted with a disinfecting composition, e.g., aqueous solution, according to the present invention, preferably at a temperature in the range of about 0° C. to about 100° C., more preferably in the range of about 10° C. to about 60° C. and still more preferably in the range of about 15° C. to about 30° C. Contacting at or about ambient temperature is very convenient and useful. The contacting preferably occurs at or about atmospheric pressure. The contacting preferably occurs for a time to substantially disinfect the lens being treated. Such contacting times can be in the range of about 1 minute to about 12 hours or more.

After this contacting, the disinfected contact lens can be taken from the composition and placed directly in an eye, e.g., a human eye, for safe and comfortable wear. Alternately, after being disinfected, the contact lens can be contacted with a second medium, e.g., a liquid aqueous medium such as a preserved isotonic saline solution, prior to being placed in the eye of the wearer of the disinfected contact lens.

The contact lens care compositions disclosed herein are adaptable for use in most types of contact lens care equipment, such as ultrasonic cleaners and the like.

The following examples are set out to illustrate, but not limit, the scope of this invention.

EXAMPLES 1 TO 4

A series of four (4) compositions are prepared by blending the constituents together. These compositions are as follows:

| CONSTITUENT | COMPOSITION[2] [3] | | | |
|---|---|---|---|---|
| | 1 | 2 | 3 | 4 |
| Commercially available grapefruit seed extract, wt. % | 0.1 | 1 | 0.1 | 1 |
| Disodium ethylene diamine tetraacetate, wt. % | | 0.1 | 0.1 | 0.1 |
| Sodium chloride, wt. % | 0.7 | 0.6 | 0.6 | 0.6 |
| Boric acid, wt. % | 0.4 | 0.4 | 0.4 | 0.4 |
| Sodium borate Decahydrate NF, wt. % | 0.2 | 0.2 | 0.2 | 0.2 |
| Nonionic surfactant[1] wt. % | | 0.1 | | |
| Hydroxyethyl cellulose NF, wt. % | | | | 0.4 |
| Purified water, USP | QS | QS | QS | QS |

[1]A nonionic surfactant containing polyoxyethylene-polyoxypropylene block copolymer and sold under the trademark Pluronic F 127 by BASF Wyandotte Corporation.
[2]Hydrochloric acid and sodium hydroxide are added to give a pH within the range of 6.8 to 7.6.
[3]Composition 1 is formulated as a borate buffered saline solution. Composition 2 is formulated as a soft contact lens disinfecting and cleaning solution. Composition 3 is formulated as an eye rewetting solution. Composition 4 is formulated as a soft contact lens disinfecting solution.

Each of these compositions is tested for preservative efficacy and passes the USP preservative efficacy criteria.

These results demonstrate that grapefruit seed extract is an effective antimicrobial preservative for contact lens care products. Composition 4 is quite effective as a contact lens disinfecting solution in a standard contact lens care regimen, with or without simultaneous or sequential enzymatic lens cleaning as part of the regimen.

EXAMPLE 5

Composition 4, described above, is used to disinfect a conventional soft contact lens as follows. 10 ml of the composition is provided at room temperature. The contact lens to be disinfected is placed in the composition. Four hours after the contact lens is first introduced into the composition, it is removed from the composition and placed directly into the wearer's eye. It is found that after four hours, the contact lens is effectively disinfected. Also, the lens wearer experiences no discomfort or eye irritation from wearing the disinfected contact lens. Alternately, after the contacting for four hours noted above, the disinfected contact lens is rinsed with preserved or non-preserved sterile isotonic saline solution prior to placing the disinfected lens in the wearer's eye. The lens wearer experiences no discomfort or eye irritation from wearing the disinfected contact lens.

EXAMPLE 6

Example 5 is repeated except that about 50 ppm by weight of subtilisin A, based on the total weight of the Composition 4 used, is added at the same time the contact lens to be disinfected is added to the composition. Four hours after the contact lens is first introduced into the composition, it is removed from the composition, rinsed with Composition 4, or with preserved or non-preserved sterile isotonic saline solution, and placed directly into the wearer's eye. It is found that after four hours, the contact lens is effectively disinfected and cleaned of protein-based debris. Also, the lens wearer experiences no discomfort or eye irritation from wearing the disinfected and cleaned contact lens.

While this invention has been described with respect to various specific examples and embodiments, it is to be understood that the invention is not limited thereto and that it can be variously practiced within the scope of the following claims.

What is claimed is:

1. A method for disinfecting a contact lens comprising:
   contacting a contact lens with a composition comprising a liquid aqueous medium having an ophthalmically acceptable pH and an effective disinfecting amount of grapefruit seed extract in the range of about 0.001% to about 5% by weight per volume of said liquid aqueous medium at conditions effective to disinfect said contact lens, said grapefruit seed extract including essential oils which exhibit antimicrobial activity in said composition.

2. The method of claim 1 wherein said contact lens after being disinfected is contacted with a second liquid aqueous medium prior to being placed in the eye of the wearer of said contact lens.

3. The method of claim 1 which further comprises contacting said contact lens in a liquid medium with at least one enzyme capable of removing debris from a contact lens in an amount effective to remove debris from said contact lens.

4. The method of claim 3 wherein said contact lens-grapefruit seed extract contacting and said contact lens-enzyme contacting occur at substantially the same time.

5. The method of claim 1 wherein said grapefruit seed extract is the sole antimicrobial component in said composition.

6. The method of claim 1 wherein said ophthalmically acceptable pH is in the range of about 6.8 to about 7.6.

7. A method for preserving an ophthalmically acceptable medium comprising:
contacting an ophthalmically acceptable aqueous medium including an effective pH buffering amount of a buffer component with an effective preserving amount of grapefruit seed extract in the range of about 0.001% to about 5% by weight per volume of said ophthalmically acceptable aqueous medium at conditions effective to preserve said ophthalmically acceptable aqueous medium and thereby form a preserved product having an ophthalmically acceptable pH, said grapefruit seed extract including essential oils which exhibit antimicrobial activity in said composition.

8. The method of claim 7 wherein said ophthalmically acceptable aqueous medium is substantially non-oxidative and is useful in caring for a contact lens, and said ophthalmically acceptable pH is in the range of about 6.8 to about 7.6.

9. The method of claim 7 wherein said ophthalmically acceptable aqueous medium is a liquid aqueous medium.

10. The method of claim 7 wherein said grapefruit seed extract is the sole antimicrobial component in said composition.

11. A composition useful for disinfecting a contact lens comprising a liquid aqueous medium having an ophthalmically acceptable pH and, included therein, an effective contact lens disinfecting amount of grapefruit seed extract in the range of about 0.001% to about 5% by weight per volume of said compositions and an effective pH buffering amount of a buffer component, said grapefruit seed extract including essential oils which exhibit antimicrobial activity in said composition.

12. The composition of claim 11 which further comprises an effective amount of a tonicity adjustor component, said composition is ophthalmically acceptable, and said ophthalmically acceptable pH is in the range of about 6.8 to about 7.6.

13. The composition of claim 11 which further comprises an effective amount of a wetting component.

14. The composition of claim 11 which further comprises at least one enzyme capable of removing debris from a contact lens in an amount effective to remove debris from a debris laden contact lens.

15. The composition of claim 11 in which said grapefruit seed extract is the sole antimicrobial component.

16. A preserved composition comprising an ophthalmically acceptable aqueous medium having an ophthalmically acceptable pH and, included therein, an effective preserving amount of grapefruit seed extract in the range of about 0.001% to about 5% by weight per volume of said composition and an effective pH buffering amount of a buffer component, said grapefruit seed extract including essential oils which exhibit antimicrobial activity in said composition.

17. The preserved composition of claim 16 which further comprises an effective amount of a tonicity adjustor component, and wherein said ophthalmically acceptable pH is in the range of about 6.8 to about 7.6.

18. The preserved composition of claim 16 which further comprises an effective amount of a wetting component.

19. The preserved composition of claim 16 which further comprises a polymeric wearability component in an amount effective to enhance the wearability of a contact lens contacted with said composition.

20. The preserved composition of claim 16 in which said grapefruit seed extract is the sole antimicrobial component.

* * * * *